United States Patent [19]
Koskinen et al.

[11] Patent Number: 5,908,964
[45] Date of Patent: Jun. 1, 1999

[54] PROCESS FOR PREPARING ALKYL ETHERS AND MIXTURES THEREOF

[75] Inventors: Matti Koskinen, Helsinki; Petri Lindqvist, Porvoo; Harri Järvelin; Juhani Aittamaa, both of Helsinki, all of Finland

[73] Assignee: Neste Oy, Espoo, Finland

[21] Appl. No.: 08/803,177

[22] Filed: Feb. 19, 1997

[30] Foreign Application Priority Data

Feb. 22, 1996 [FI] Finland ..................... 960813

[51] Int. Cl.$^6$ ..................... C07C 41/06
[52] U.S. Cl. ............ 568/697; 568/699; 203/29; 203/45; 203/75
[58] Field of Search ............... 568/697, 698, 568/699; 203/29, 45, 75

[56] References Cited

U.S. PATENT DOCUMENTS 5,536,886  7/1996  Tamminen ............... 568/697

Primary Examiner—Shailendra Kumar
Assistant Examiner—Sreeni Padmanabhan
Attorney, Agent, or Firm—Birch, Stewart, Kolasch & Birch, LLP

[57] ABSTRACT

The invention concerns a process for preparing a tertiary alkyl ether product. The process comprises reacting the isoolefins of an olefinic hydrocarbon feedstock in a reaction zone (1–3) with an alkanol to form a reaction mixture, which is subjected to distillation in a first distillation zone (4). The bottoms product of the first distillation contains the ether(s), whereas the overhead stream contains unreacted alkanol and a mixture of light hydrocarbons. The overhead stream is subjected to a second distillation in a second distillation zone (15). The overhead product of the second distillation mainly contains the lightest hydrocarbons and a small amount of alkanol, and the bottoms product contains an essentially oxygenate-free hydrocarbon stream which can be used as such for alkylation. In order to increase the conversion of the process, a side drawoff is withdrawn from the second distillation zone (15) and recirculated to the reaction zone (1-3).

37 Claims, 3 Drawing Sheets

PROCESS FOR PREPARING ALKYL ETHERS AND MIXTURES THEREOF

BACKGROUND OF THE INVENTION

1. Field of the Invention

The present invention relates to the preparation of tertiary alkyl ethers. In particular, the invention concerns a novel process for preparing such ethers, wherein isoolefins, in particular $C_4$–$C_7$ isoolefins of an olefinic hydrocarbon feedstock are reacted with a suitable alkanol to prepare the corresponding ethers. These ethers are recovered and, if necessary, further processed in order to prepare, e.g, a motor fuel component or a petrochemical feedstock. A hydrocarbon stream of unreacted hydrocarbons emanating from the etherification reaction is subjected to alkanol recovery and oxygenate-removal enabling direct use of hydrocarbon effluent for another process, such as alkylation.

2. Description of Related Art

Tertiary alkyl ethers improve the anti-knocking characteristics of motor fuels and reduce the concentration of detrimental components in the exhaust gases. Of the alkyl tert-alkyl ethers used as components of motor fuels, the following can be mentioned: methyl t-butyl ether (MTBE), ethyl t-butyl ether (ETBE), t-amyl methyl ether (TAME), t-amyl ethyl ether (TAEE) and t-hexyl methyl ether (THME). These ethers are produced by etherification of an isoolefin with a monovalent aliphatic alcohol (in the following also called an "alkanol"). The isoolefin feedstock can comprise pure $C_4$ or $C_5$ components or a mixed hydrocarbon feedstock containing a range of $C_3$–$C_7$ and heavier hydrocarbons. Typically ion exchange resins are used as etherification catalysts.

In the conventional etherification processes, ethers are produced in a series of reactors to which a mixture of isoolefins and an alkanol are fed. The ether product is separated from the reaction mixture by ordinary distillation. The bottom product of the distillation process comprises the ether(s) and, depending on the process, also some of the unreacted heavier hydrocarbons. The overhead stream consists of an unreacted alkanol together with some lighter hydrocarbons, dialkyl ethers and, possibly, water.

Before the unreacted hydrocarbons in the overhead stream can be used for chemical processing by, say, alkylation, it has to be freed from oxygenates and other contaminants. Thus, the concentration of alkanols and other oxygenated hydrocarbons, such as dialkyl ethers, has to be reduced to below 100 ppm, preferably below 50 ppm. According to conventional technology, this separation and decontamination operation requires rather complex process steps. To take MTBE production as an example, it can be noted that the overhead from the reaction product distillation, containing methanol-rich $C_4$'s, is first washed in a countercurrent liquid-liquid extraction column with water to form a methanol-water solution. This solution is recovered from the bottom of the extraction column and fed into a fractionation tower, wherein methanol is recovered. The $C_4$ raffinate from the extraction column is then fed into another fractionation tower, called the oxygenate removal unit, in order to separate the light oxygenates such as dialkyl ethers, trace alkanol and water from the $C_4$ raffinate. Thus, one extraction column and two distillation columns are required to recover the methanol and to produce an essentially oxygenate-free $C_4$ raffinate. Moreover, the purification of the unreacted hydrocarbons in the overhead stream typically requires the use of an oxygenated compound, water, which just after introduction must be carefully removed from the raffinate.

Alternatively, a specific molecular sieve system may be employed for oxygenates removal.

It is known in the art of TAME production (PCT Patent Application No. WO 93/1903) that the amount of alkanol in the overhead stream can be minimized by operating the fractioning in such a way that most, and preferably practically (nearly) all, of the alkanol in the distillate is bound to $C_4$ hydrocarbons, forming an azeotrope with them. Such a product can be blended with fuels often without any additional purification steps. However, because the amount of alkanols in the overhead stream depends on the amount of unreacted $C_4$'s of the reaction mixture, the overhead stream obtained from etherification of an isobutylene feed according to the above art will contain too much alkanol for most of the downstream processes, in particular alkylation.

SUMMARY OF THE INVENTION

The present invention aims at eliminating the problems associated with the prior art and providing a completely novel process for producing tertiary alkyl ethers.

The invention is based on the concept of operating the separation distillation of a an etherification process in such a way that the overhead product comprises unreacted hydrocarbons and unreacted alkanol. In order to reduce the amount of oxygenates in the overhead stream, this stream is subjected to a second distillation. To increase the conversion, a side drawoff is taken from the second distillation and recirculated to the etherification.

In particular, the present process comprises the steps of reacting isoolefifis of an isoolefrnic hydrocarbon feedstock containing at least two groups of $C_{3-7}$ hydrocarbons having different carbon numbers in a reaction zone with at least one alkanol to form an ether-containing reaction mixture, subjecting said ether-containing reaction mixture to distillation in a first distillation zone, recovering an ether product from the bottom of the first distillation zone, withdrawing an overhead stream from the first distillation zone containing unreacted alkanol and a mixture of hydrocarbons comprising at least the two lightest hydrocarbon groups present in the feedstock, conducting the overhead stream to a second distillation zone and subjecting it to distillation, withdrawing from the second distillation zone an overhead product, which contains the lightest hydrocarbons of the overhead stream of the first distillation zone and the minimum amount of alkanol typically due to azeotropic behaviour of the mixture, withdrawing a side drawoff from the second distillation zone and recirculating it to the reaction zone, and recovering a bottoms product from the second distillation zone.

The invention comprises three particularly preferred embodiments for preparing methyl and ethyl ethers. Two of the preferred embodiments concern the preparation of pure ether products and one the preparation of mixed ethers. The ether products are characterized as "pure" in the sense that they primarily contain only one type of ether (purity usually at least about 99.5 wt-%).

The alternative process for producing pure methyl t-butyl ether (MTBE) and/or ethyl t-butyl ether (ETBE), comprises the steps of subjecting an olefmic hydrocarbon mixture containing isobutylene and some, preferably at least 0.1 wt-%, $C_3$ hydrocarbons to etherification with methanol or ethanol, respectively, in etherification reactor(s) to form a reaction mixture, recovering the reaction mixture and conducting it to a first distillation zone, wherein it is subjected to distillation, recovering from the first distillation zone a bottoms product containing the tertiary butyl ether, withdrawing from the first distillation zone a overhead stream containing a mixture of unreacted $C_3$ and $C_4$ hydrocarbons and unreacted alkanol, subjecting the overhead stream to distillation in a second distillation zone, withdrawing an overhead product of the second distillation containing a mixture of unreacted $C_3$ hydrocarbons together with unreacted alkanol, the latter being present in the minimum amount typically dictated by the azeotropic behaviour of the mixture, and recovering from the second distillation zone a bottoms product containing an essentially oxygenate-free $C_4$ hydrocarbon fraction.

The alternative process for producing an ether product essentially containing t-amyl methyl ether (TAME) and/or t-amyl ethyl ether (TAEE), comprises the steps of subjecting an olefinic hydrocarbon mixture containing isoamylenes and some, at least 0.1 wt-%, $C_4$ hydrocarbons to etherification with methanol or ethanol, respectively, in etherification reactor(s), to form a reaction mixture, recovering the reaction mixture and conducting it to a first distillation zone, wherein it is subjected to distillation, recovering from the first distillation zone a first bottoms product containing the tertiary amyl ether, withdrawing a first overhead stream containing a mixture of unreacted $C_4$ and $C_5$ hydrocarbons and unreacted alkanol, subjecting the overhead stream of the first distillation zone to distillation in a second distillation zone, recovering from the second distillation zone a bottoms product containing an essentially oxygenate-free $C_5$ hydrocarbon fraction, and withdrawing an overhead product containg a mixture of unreacted $C_4$ hydrocarbons and alkanol, the latter at the minimum amount typically dictated by the azeotropic behaviour of the mixture.

The alternative process for producing an ether product containing a mixture of tertiary alkyl ethers (MTBE and TAME and possibly heavier methyl ethers, and/or ETBE and TAEE and possibly heavier ethyl ethers) comprises subjecting an olefinic $C_3$ to $C_7$ hydrocarbon mixture containing reactive isoolefins to etherification with methanol or ethanol in a reaction zone to form a reaction mixture containing tertiary $C_4$ to $C_7$ alkyl ethers, recovering the reaction mixture and conducting it to a first distillation zone, wherein the reaction mixture is subjected to distillation, recovering from the first distillation zone a bottoms product containing ethers and $C_{5+}$ hydrocarbons, withdrawing from the first distillation zone an overhead stream mainly containing a mixture of unreacted $C_3$ to $C_4$ hydrocarbons and unreacted alkanol, the alkanol being present in the minimum amount typically due to azeotropic behaviour of the mixture, withdrawing a side drawoff and recirculating it to the reaction zone, subjecting the overhead product of the first distillation to distillation in a second distillation zone, recovering from the second distillation zone a bottoms product containing an essentially oxygenate-free $C_4$ hydrocarbon fraction, and withdrawing an overhead stream containing a mixture of unreacted $C_3$ hydrocarbons together with unreacted alkanol, the latter at the minimum amount dictated by the azeotropic behaviour of the mixture.

In each of the above embodiments a side drawoff is withdrawn from the second distillation zone and recirculated to the reaction zone. The second distillation zone is typically operated at a higher pressure than the first one.

This invention will provide significant advantages over the present technology. The invention will greatly simplify oxygenate removal in production of tertiary alkyl ethers. For methanol based ethers, the process produces a $C_4$-rich product which contains so little oxygenates (typically less than 20 ppm) that it can be fed directly without any oxygenate removal units to downstream processes like alkylation. For ethanol ethers, the oxygenate concentration is normally below the limit of an alkylation unit. The novel process typically utilizes conventional equipment and catalysts. Furthermore, integration of the oxygenate removal with the etherification process as described herein enhances the overall conversion of the etherification unit. In particular, when $C_{4+}$ olefnic hydrocarbon streams are processed extremely high conversion rates are obtained (over 99% ) giving significant advantages over the traditional etherification processes (conversion rates in the range of 91 to 96% ). The losses of the valuable $C_4$ olefins are practically negligiable. An important advantage is illustrated by the above mentioned alternative processes: the present invention makes it possible simultaneously to process in one and the same process unit an integral feedstock containing all light isoolefins from an FCC unit. The new process can also be used for producing pure ether products. Finally, the present invention reduces the accumulation of harmful catalyst poisons.

BRIEF DESCRIPTION OF THE DRAWINGS

In the following the invention will be examined in more detail with reference to the attached drawings of which

DETAILED DESCRIPTION OF THE INVENTION

According to the present invention, the production of the tertiary alkyl ethers can be carried out in a conventional etherification system comprising one or more reactors connected to process equipment for product separation. This embodiment is illustrated by the attached drawings.

However, the invention can also be performed in a "catalytic distillation reactor system", wherein the etherification reaction and the separation of the products take place at least partially simultaneously. Such an apparatus typically comprises either a conventional "reactive distillation column" or a distillation column combined with at least one side reactor. Reactive distillation for ether production is well-known in the art and described in, e.g., U.S. Pat. Nos. 4,307,254, 4,336,407, 4,443,559, 4,504,687, 4,978,807, 3,629,478, 4,487,430, 4,847,431, 5,013,407, 5,026,459, 4,925,989 and 4,918,244, the contents of which are herewith incorporated by reference.

In the "side reactor" process configuration, the hydrocarbons and the alkanol are fed into a side drawoff of a distillation column used for product separation. The side draw is conducted to at least one side reactor, connected to the distillation column. Having passed the side reactor(s) the reaction mixture is returned to the distillation column, preferably at a point below the feed point. Side reactor embodiments are described in more detail in International Patent Applications WO 93/19031 and WO 93/19032.

As will become obvious from the following description, any one of the distillation columns used can be replaced totally or partly by a catalytic distillation column. The term "reaction zone" denotes any zone wherein the isoolefrns and the alkanol(s) react to form ethers. In the embodiment illustrated in the Figures, the "reaction zone" comprises the catalyst beds of the three reactors. If a catalyst bed has been arranged in one or more of the distillation towers, that bed is also included in the "reaction zone" concept.

Suitable hydrocarbon feedstocks for preparing tertiary alkyl ethers are, for example, the following: FCC gasoline, FCC light gasoline, FCC liquefied petroleum gas, Pyrolysis $C_5$ gasoline, $C_4$ stream (raffinate 1) from steam cracking unit, olefmic $C_4$ stream from a butane dehydrogenating unit, TCC gasoline, $C_4$ stream from TCC, RCC gasoline, $C_4$ stream from RCC, coker gasoline or $C_4$ stream originating from a coking unit or a mixture of these. An example of a preferred feedstock is Fluidized Catalytic Cracking (FCC) Gasoline containing $C_{4-7}$ hydrocarbons, a substantial portion, generally at least 5% typically about 7 to 30 wt-%, of which comprises reactive $C_{4-7}$ isoolefins.

Before the etherification reaction the hydrocarbon feedstock can be subjected to a pretreatment in order to remove impurities and to increase the amount of reactive isoolefins. Acidic residues can be removed by washing the feedstock with water and multi-unsaturated olefins can be selectively hydrogenated in the presence of a catalyst to form mono-unsaturated compounds.

The aforementioned hydrocarbon compositions generally contain light, volatile $C_{2-4}$ hydrocarbons. These hydrocarbons reduce the relative volatility of the alkanol in the second distillation zone. If the hydrocarbon compositions do not contain enough (>0.1 wt-%) of such light compounds for practical operation of the second distillation zone as required by the present invention, these hydrocarbons can be separately added and fed into the process. This feed can be directed into the reaction zone together with the rest of the hydrocarbon feed or the light hydrocarbons can be introduced into the first distillation zone or to any suitable location within the process.

The "reactive isoolefins" which take part in the etherification reactions include, for example, the following compounds: isobutylene, 2-methyl-1-butene, 2-methyl-2-butene, 2-methyl-1-pentene, 2-methyl-2-pentene, 2,3-dimethyl-1-butene, 2,3-dimethyl-2-butene, 2-ethyl-1-butene, 2-methyl-2-hexene, 2,3-dimethyl-1-pentene, 2,3-dimethyl-2-pentene, 2,4-dirnethyl-1-pentene, 2-ethyl-1-pentene and 2-ethyl-2-pentene.

The term "hydrocarbon group" used herein denotes all hydrocarbons having the same number of carbon atoms. Thus, for example, butanes and butenes and other hydrocarbons with four carbon atoms belong to the same group, called $C_4$ hydrocarbons, whereas the pentanes and pentenes belong to another group which is called $C_5$ hydrocarbons.

The "alkanol" used for etherification of the isoolefins includes lower alkyl alcohols having 1 to 6 carbon atoms. They should also be capable of forming azeotropes with the saturated and unsaturated hydrocarbons, in particular the $C_{2-7}$ hydrocarbons, of the hydrocarbon feedstock. As specific examples of the alkanols, the following can be mentioned: methanol, ethanol, n-propanol, i-propanol, n-butanol, i-butanol and t-butanol. Methanol and ethanol are particularly preferred. In the etherification reaction, mixtures of two or more alkanols can be used in addition to pure alkanols.

In the present context and used with reference to mixtures of an alkanol and hydrocarbons, "azeotropic mixture" means a mixture wherein the alkanol concentration corresponds to a solution of two or more liquids, the composition of which does not change significantly upon distillation. The alkanol is removed in an amount typically due to azeotropic behaviour of the mixture. This amount is 0.05 to 30, preferably about 0.1 to 15 and in particular about 0.5 to 5 wt-%, calculated from the weight of the mixture.

The overhead product of the second distillation zone "mainly" contains the lightest hydrocarbons of the overhead stream of the first distillation zone, which means that about 60 to 99, preferably 80 to 98, in particular 85 to 95 wt-% of said stream is comprised of the light hydrocarbons. The overhead product can contain not only the lightest hydrocarbons of the azeotrope but also some hydrocarbons from the second lightest hydrocarbon group.

In addition to tertiary alkyl ethers also other oxygeneous compounds, such as dialkyl ethers, are formed during the etherification reaction. Furthermore, such compounds may be present in the feedstock. The term "oxygenates" is used to designate oxygen-containing compounds in the reaction mixture. In addition to the ethers and corresponding organic compounds also water is considered an oxygenate for the purpose of this invention.

In many of the embodiments, the bottoms product of the second column is characterized as being "essentially" oxygenate-free, which means that it contains less than 1000 ppm, preferably less than 50 ppm, and in particular less than 30 ppm, of oxygenates.

According to the invention, any catalyst typically used in etherification processes can be employed. Conventional cation exchange resin is typically the preferred catalyst, but also other kinds of homogeneous or heterogeneous catalysts may be utilized, e.g. zeolites.

The cation exchange resin may contain sulfonic acid groups and it can be obtained by polymerization or copolymerization of aromatic vinyl compounds followed by sulfonation. Examples of aromatic vinyl compounds suitable for preparing polymers of copolymers are: styrene, vinyl toluene, vinyl naphthalene, vinyl ethyl-benzene, methyl styrene, vinyl chlorobenzene and vinyl xylene. The acid cation exchange resin typically contain some 1.3 to 1.9 sulfonic acid groups per aromatic nucleus. Preferred resins are based on copolymers of aromatic monovinyl compounds with aromatic polyvinyl compounds, particularly, divinyl compounds, in which the polyvinyl benzene content is from about 1 to 20 wt-% of the copolymer. The ion exchange resin preferably has a granular size of about 0.15 to 1 mm. In addition to the above resins perfluorosulfonic acid resins, which are copolymers of sulfonyl fluorovinyl ethyl and fluorocarbon, can be used.

Turning now to the embodiments shown in the attached drawing, the invention will be described in more detail. The following description will deal mainly with the embodiment shown in FIG. 1, which is suitable for preparing a mixture of alkyl ethers.

Figure 1:
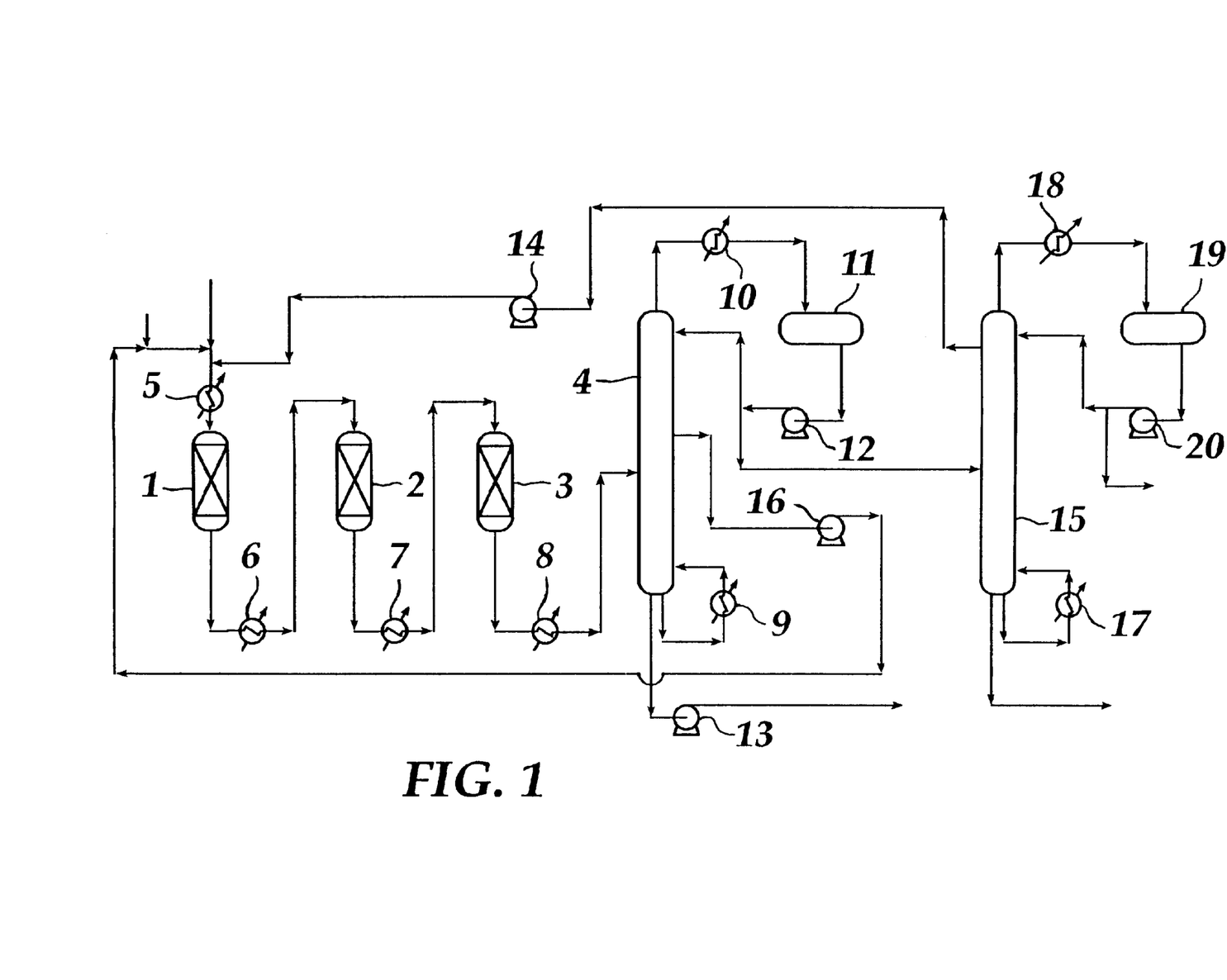
FIG. 1 shows in a schematic fashion the simplified configuration of a process for preparing a product containing a mixture of $C_4$, $C_5$ and possibly heavier tertiary alkyl ethers.

Reference numerals 1–3 designate reactors, 4 and 15 distillation towers, 5–10, 17 and 18 heat exchangers, 11 and 19 reflux drums, and 12–14 and 16 and 20 pumps.

According to the present invention, products containing mixtures of $C_4$ and $C_5$ and possibly heavier ethers can be produced in a system comprising a reaction section with one or a more reactors 1–3 in cascade or in parallel with a follow-up distillation section (in the following also called the "fractionation section") comprising distillation columns 4 and 15 designated for product purification and for recovery of unreacted alkanols and reactive olefins.

Typically, in this configuration, the hydrocarbon feed stream containing reactive olefins, the alkanol (preferably methanol or ethanol) feed stream and at least one recycle stream from the fractionating section are fed into the reaction section 1–3. The feed streams are either mixed before the reaction section or separately fed into the first etherification reactor 1. Some or all of the feeds can be adjusted to a proper temperature for etherification either before the reactor (by heat exchanger 5) or the required reaction temperatures are adjusted in the reactor construction itself.

The etherification reaction can be carried out in many different reactor types designed to contain a proper amount of suitable catalyst needed for the reaction between the reactive olefm(s) and the alkanol(s). The reactor construction can be of conventional fixed bed type in which the catalyst is placed in one or more catalyst beds or in tubes with or without heat transfer equipment. Other configurations such as fluidized beds, ebullated beds or a combination of any reactors containing the necessary catalyst are possible. The reaction can also be carried out inside a catalytic distillation tower (catalytic distillation reactor), as mentioned above.

Reaction temperature can be controlled by adjusting the temperature of the feed for one or all of the reactors to the proper value, by putting cooling/heating devices inside the reactor, or by controlling the concentration of reactive olefins in the feed stream by manipulating either one or both of the recycle streams stemrning from the fractionation section. The effluent from the first reaction stage is often cooled in a heat exchanger 6 and fed to another reaction zone 2 to improve the overall conversion of the reactive components. This may be followed by further reaction zones 3 operating typically at descending temperature levels compared to the previous one.

The temperature can also be controlled by adjusting the pressure and removing heat by vaporising part of the content of the reactor.

When processing a combined hydrocarbon stream containing $C_{3-7}$ olefinic feedstocks the fresh hydrocarbon feed is typically mixed with all recycle hydrocarbon/ alkanol streams and alkanol and fed to the first reaction zone 1 at a suitable temperature. As above, this stage is normally followed by a heat exchanging device 6 in which the reaction effluent is cooled to a suitable temperature so that it can be fed to another reaction zone 2 to further improve the conversion of both reactive hydrocarbon species and the alkanols present in the feed. This processing scheme, lowering reaction effluent temperature after the previous reaction zone (reactor 2 and heat exchanger 7; reactor 3 and heat exchanger 8) before feeding it to another, can be repeated several times before the reaction zone effluent is fed to a distillation column, which may also contain catalytic material to further improve the conversion.

Fractionation in the first distillation zone is carried out in such a way that only the two lightest hydrocarbon groups present in significant amounts in the original feed mixture are taken overhead as a distillate together with unreacted alkanol typically in azeotropic concentration with the hydrocarbons. In the current example this means that the overhead of the first distillation zone contains an azeotropic or near azeotropic mixture of $C_{3-4}$ hydrocarbons and the feed alkanol. In order to minimize the amount of alkanol in the hydrocarbon-alkanol-azeotrope, only the $C_{3-4}$ hydrocarbon-alkanol-azeotropes in the present example are taken as an overhead product, the rest of the alkanol is taken out as a sidestream or consumed in chemical reaction within the tower. This sidestream contains most of the alkanol present in the column feed and also a significant amount of hydrocarbons. Typically this sidestream contains at least 30 wt-%, preferably at least 70 wt-% and in particular over 90% of the total alkanol feed to the second distillation zone. Some heavier hydrocarbons may end up in the distillate as impurities, typically in concentrations less than 20%.

The azeotrope of the overhead product is beneficial for the process. If suitable amounts of any light component needed for the azeotrope are not present in the original feed stream, such a component may be added to the feed of the distillation tower or in any suitable location within the tower itself or in any suitable location within the process.

The pressure in the tower 4 is typically adjusted to a level suitable for condensing the distillate. Typical pressure in processing $C_{3-7}$ cut in a petroleum refmery or petrochemical plant is below 10 bars, depending on the relative amount of light hydrocarbons present in the feed stream.

From the same distillation column a sidestream is taken and fed to the reaction zone. It is typically mixed with fresh hydrocarbon and alkanol feeds mentioned above and with any additional recycle feed coming from other fractionation towers within the unit. The side drawoff from distillation tower 4 comprises some 1 to 1000%, preferably about 50 to 200% of the fresh feed. The pressure of the side stream may be increased by a pump 16 as the distillation is often carried out at a lower pressure than the etherification reaction, if said reaction is not carried out within the distillation tower itself. The sidestream can also be fed to any location within the reaction zone, for example between the first and second reactors 1, 2, if feasible.

According to the preferred embodiment of the present process the distillation tower 4 is operated in such a way that only alkanol in azeotropic concentration is allowed in the distillate with the light hydrocarbons present in the feedstock. The main bulk of the feed alkanol is heavier than the hydrocarbons going overhead at the top of the column. Therefore the alkanol not bound to the distillate hydrocarbons in form of an azeotrope will tend to flow downwards within the column. At the same time the vapor-liquid equilibrium between $C_5$ and heavier hydrocarbons and the alkanol at the bottom of the column is maintained in such concentrations that the bottom product is essentially free of any alkanols, which causes the alkanol not boiling over in the tower to concentrate in the side stream. Thus the alkanol will concentrate between the top and the bottom of the tower. By carefully choosing the right location of the sidestream and conducting the stream through reaction section, typically preceding the distillation, an alkanol consuming etherification reaction can be created with suitable catalyst, which will enhance the overall alkanol conversion of the processing unit. Additionally, catalytic material may be placed in the tower itself or in the sidestream, to augment or substitute any additional reaction that could be generated within the reaction section treating the fresh feed.

The bottom product of distillation tower 4 contains, e.g., $C_{4-7}$ tertiary ethers formed and $C_{5+}$ hydrocarbons.

The first distillation step is followed by another distillation, marked with reference numeral 15 in the attached drawings. The second distillation tower will fractionate the distillate of tower 4. This separation is characterized by application of azeotropic phenomena in the top of the tower, which results from the generation of a hydrocarbon-alkanol azeotrope between the lightest hydrocarbon present in significant amounts in the original hydrocarbon feed and the alkanol. The lightest hydrocarbon in this context means one single type of hydrocarbon or a group of hydrocarbons having the same carbon number. Only the lightest hydrocarbon and the azeotropic concentration of alkanol is taken out of the tower as an overhead product. In the current example this means that in order to minimize the amount of alkanol in the hydrocarbon-alkanol-azeotrope, only the $C_3$-hydrocarbon-alkanol-azeotropes are taken as an overhead product, the rest of the alkanol is taken out as a sidestream or consumed in chemical reaction within the tower. Some heavier hydrocarbons may end up in the distillate as impurities, typically in concentrations less than 20%.

According to the present process the distillation tower 15 is operated in such a way that only alkanol in azeotropic concentration is allowed in distillate with the lightest group of hydrocarbons present in the feedstock. This stream normally contains side reaction products such as dimethyl ether and water. Therefor, the bottoms product of the tower is essentially oxygenate-free.

If suitable amounts of any light component needed for the overhead product are not present in the original feed stream, such a component may be added to the feed of the distillation tower or in any suitable location within the tower itself or in overhead or reboiling equipment of the column or in any suitable location within the process. The main bulk of the alkanol in the tower 15 is heavier than the hydrocarbons going overhead at the top of the column. Therefore the alkanol not bound to the distillate hydrocarbons in form of an azeotrope will tend to flow downwards within the column. At the same time the vapor-liquid equilibrium between $C_4$ and some heavier hydrocarbons present in the tower feed and the alkanol at the bottom of the column is maintained in such concentrations that the bottom product is essentially free of any alkanols, which causes the alkanol not boiling over in the tower to concentrate in the side stream. Thus, the alkanol will concentrate between the top and the bottom of the tower. By repeating the previously stated principle of carefully choosing the right location of the sidestream and conducting the stream through reaction section or part of it, typically preceding the first distillation zone, an alkanol consuming etherification reaction can be created with suitable catalyst, which will enhance the overall alkanol conversion of the processing unit. The underlying reason is that this stream contains most of the alkanol present in the column feed and also a significant amount of hydrocarbons. Typically this sidestream contains at least 30 wt-%, preferably at least 70 wt-% and in particular over 90% of the total alkanol feed to the second distillation zone. The recycling of this stream will result in improved iso-olefin and alkanol conversion within the whole process unit. Additionally, catalytic material may be placed in the second distillation tower itself or in the sidestream, to augment or substitute any additional reaction that could be generated within the reaction section treating the fresh feed.

The pressure in the tower is typically adjusted to a level suitable for condensing the distillate. Typical pressure in processing $C_{3-7}$ cut in a petroleum refinery or petrochemical plant is above 10 bars without refrigeration equipment, depending on the relative amount of light hydrocarbons present in the feed stream. In the present example, the pressure level in the second distillation column is maintained at higher level than in the first one. Preferably the pressure difference is at least 1 bar, in particular at least 4 bar. This has an important consequence for the process: The hydrocarbon-alkanol mixture recovered as a distillate in azeotropic concentration from the first unit can be separated in the second unit in such a way that practically alkanol free product stream is taken out as a bottom product. This is due to the fact that the higher pressure level in the second tower effectively shifts the azeotropic point to a higher alcohol concentration as shown in the following table.

TABLE 1

Ethanol/methanol-isobutane azeotrope (ref. Leu and Robinson J. Chem.Eng.Data 37, 10 (1992) and Zabaloy et al. J.Chem.Eng. Data 39, (1994)

| T (°C.) | p (kPa) | Methanol (mol-%) | Ethanol (mol-%) |
|---|---|---|---|
| 0 | 159 | 0.94 | |
| 35.45 | 477 | | 0.66 |
| 45.25 | 617 | | 0.89 |
| 50 | 733 | 4.38 | |
| 90.35 | 1671 | | 2.4 |
| 100 | 2190 | 11.17 | |

The pressure dependence of the light hydrocarbon-alkanol azeotrope ensures the separation between the components in such a way that almost completely pure hydrocarbon stream can be obtained from the bottom of the tower. In the current example, this stream contains eventually almost all of the unreacted $C_4$ hydrocarbons originally fed to the process; only minor quantity of these components will go to the bottom product of the first tower 4 or to the distillation of the second column 15.

Simultaneously, most of the other oxygenates present in the feed stream to the second distillation tower 15 will go to the distillate product of this tower. These include any water present in the feed, all light alkanols and dimethyl ether which is a by-product in methanol based ethers production. In most industrial applications this means that the resulting $C_4$ stream is almost completely free of oxygenates except for minor quantities of product ethers which may be part of the feed stream of the second unit due to incomplete separation in the first distillation tower.

Although it is preferred to operate the second distillation zone at a higher pressure than the first one, it is also possible to carry out the two distillation operations at the same pressure or even to operate the second distillation zone at a lower pressure than the first, provided that the cooling effect of the condenser is higher.

Besides separating the hydrocarbon groups and recovering the present alkanol in the side stream of the unit the second distillation column 15 performs as an oxygenate removal unit. This has a highly beneficial effect on the quality of the resulting $C_4$ stream since that stream is fully compatible with the requirements set by the most common downstream units, such as butene alkylation, catalytic oligomerization and polymerization units and some petrochemical processes (e.g. dehydrogenation).

Another possibility to utilize the key features of the present innovation is to incorporate the distillation units 4 and 15 into two different pressure zones of the same tower. The pressure zones are separated by a wall. This type of arrangement may result in savings in utility systems and in capital costs.

The present invention is suitable for processing other types of hydrocarbon feedstocks than the $C_{3-7}$ cut used in the previous example. Any combination of these can be processed in the presented processing scheme. The essential feature is to have at least a minute amount (in practice >0.1 mol- %) of some lighter component capable of forming an azeotrope with the applied alkanol besides the main feed component or groups of components subjected to etherification. The resulting azeotropic mixtures will have different compositions depending on the pressure levels used in fractionation operations and the groups of hydrocarbons and the constitution of any of such group.

Figure 3:
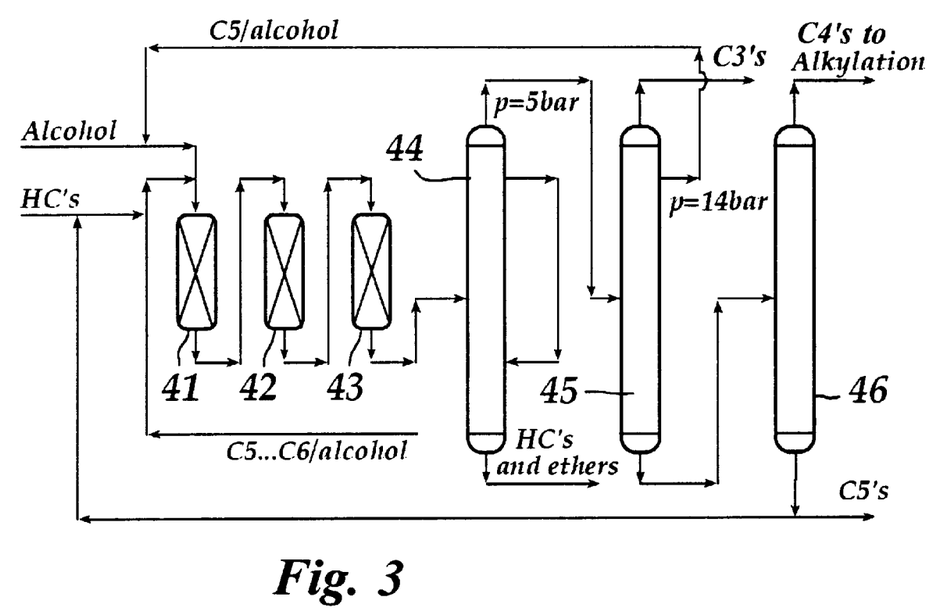
FIG. 3 shows the simplified process configuration of a process comprising three distillation columns for preparing a mixture of $C_4$ to $C_7$ ethers.

The major exception to the oxygenate removal function is diethyl ether (DEE) which is a major side product in etherification reactions based on the use of ethanol as the reactive alkanol. To separate DEE and thus to avoid accumulation of it in the alkylation feed, a third tower (depicted in FIG. 3) is foreseen. In FIG. 3 reference numerals 41–43 designate reactors and 44 to 46 distillation towers.

The $C_5$ containing hydrocarbon stream from the bottom of the second distillation column 45 is conducted to the third distillation tower 46. The separation process of the third tower 46 is a conventional one in which $C_4$ hydrocarbons go to the distillate product and DEE and heavier hydrocarbons go to the bottom stream resulting from fractionation. This stream may be combined with the bottom product of the first tower 44 or recycled as yet another recycle stream to the first reaction system 41 of the total process, in which case improved conversion for some reactive heavier hydrocarbons ($C_5$ olefins) will result in processing $C_{3-7}$ feed stream in the unit.

The above goals can be accomplished also by installing a predistillation column in front of the towers 4 and 15 of FIG. 1. The split of the incoming feed is arranged in such a way that the two lightest hydrocarbon groups present in significant concentrations ($C_{3-4}$) in the current example are recovered as distillate and fed to the second fractionator 15 and the bottom product is taken to the first tower 4 from which DEE is taken out as part of the bottom stream with ethers and the heavier hydrocarbons present in the original feed stream.

The third distillation column 46 installed after the tower 45 has also the important function of removing the required amount of C. and heavier hydrocarbons present in the bottom product of the tower 45, if this is dictated by the downstream processing units.

By using a combination of three distillation columns, it is possible to also to maintain high conversion levels while avoiding any methanol from accumulating into the alkylation feed or other process.

Figure 4:
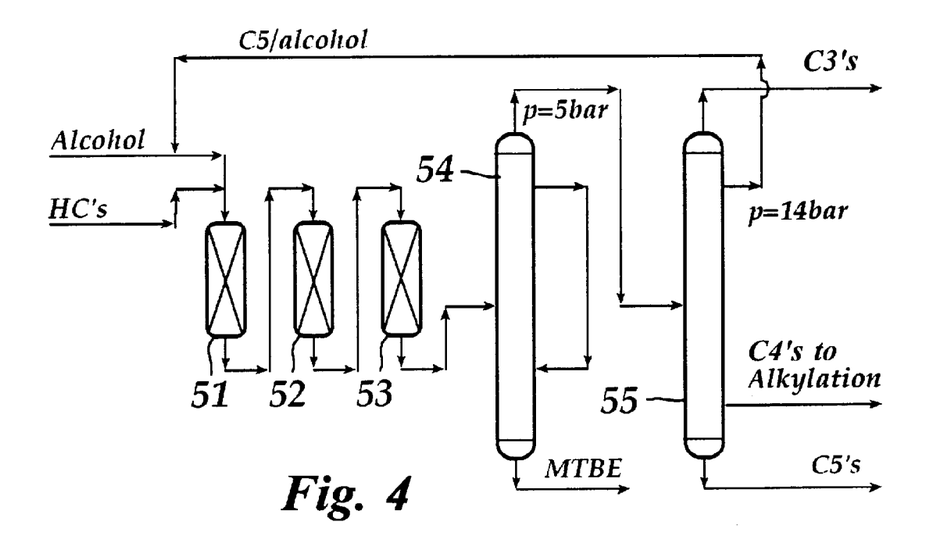
FIG. 4 shows in a schematic fashion the simplified configuration of a process, wherein the $C_4$ hydrocarbons are taken as a gaseous sidedraw of the second distillation tower.

It should be noted that the concentrations of oxygenates and $C_5$ hydrocarbons in a side drawoff taken from the second distillation zone can be so small that such a side drawoff can be used as such, i.e. without separate oxygenate removal, for alkylation, oligomerization, polymerization or dehydrogenation. Thus, in an alternative embodiment depicted in FIG.

4 the same separation process as explained above is carried out in the second distillation tower 55. Said tower differs from the tower 15 of FIG. 1 in the sense that it contains about 2 to 10, e.g., about five additional ideal trays for enhanced separation. The $C_4$ hydrocarbons can then be withdrawn in the form of a gaseous sidedraw and used, for example, as alkylation feed since the oxygenate concentration and the concentrations of $C_5$'s in the $C_4$ stream are suitably low.

Figure 2:
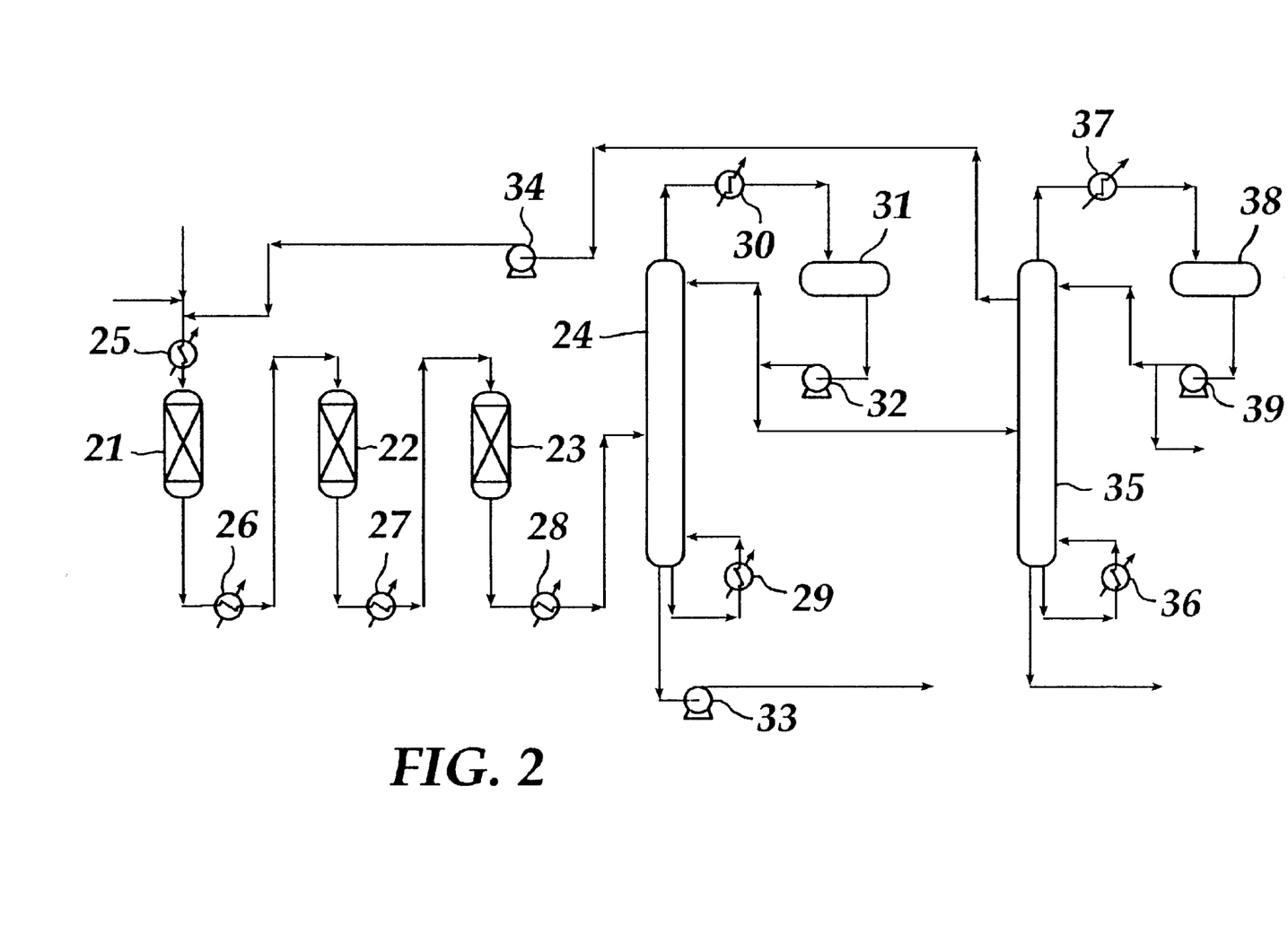
FIG. 2 depicts a simplified process scheme, which is applicable to the preparation of pure alkyl ethers, such as MTBE and TAME and the corresponding ethanol ethers.

An important application of the present invention is the production of pure ethers. FIG. 2 illustrates the underlying principles when etherifying reactive $C_4$ olefins with a suitable alkanol, preferably with methanol or ethanol. Typically such a stream contains at least minor amounts of hydrocarbons from the adjacent groups (that is $C_3$ and $C_5$ hydrocarbons or at least some $C_3$ hydrocarbons). The following description will focus on the preferred embodiment involving withdrawing an overhead stream containing a minimal amount of alkanol due to diazeotropic behaviour of the mixture of hydrocarbons and the alkanol and on operating the second distillation at a higher pressure than the first one. However, within the scope of the present invention, the embodiment of FIG. 2 can be carried out in alternative ways also, as described in connection with FIG. 1.

Reference numerals 21–23 designate reactors, 24 and 35 distillation towers, 25–30, 36 and 37 heat exchangers, 31 and 38 reflux drums, and 32–34, 37 and 39 pumps.

After carrying out etherifying in the reaction section 21–23 in an analogous way to the etherification of the previous example, the resulting effluent is taken to a distillation tower 24. The distillation is carried out in such a way that the ether product (MTBE or ETBE for methanol and ethanol based ether products respectively) is taken out as a bottom product from the tower and the unreacted $C_4$ and lighter hydrocarbons are recovered as a distillate. The alkanol will be recovered partly or totally as an overhead product. Depending on requirements and the relative amounts of $C_5$ hydrocarbons present in the feed these components may be recovered fully or partly as an overhead product.

The distillate from the first column is fed to a second distillation zone 35 in which light hydrocarbons ($C_3$'s and lighter) are recovered as an overhead product and $C_4$'s and any heavier hydrocarbons as an essentially alkanol free bottom product. If suitable amounts of the light component needed for the azeotrope are not present in the original feed stream, such a component may be added to the feed of the distillation tower or in any suitable location within the tower itself or in overhead or reboiling equipment of the column or to any suitable location in the process. The distillate contains the alkanol present in the column feed in concentrations dictated by pressure and the azeotropic constitution of the light hydrocarbon-alkanol mixture.

Analogously to the previously presented example a side stream is taken from a suitably located point in the column 35 and recycled to the reaction section 21–23 of the process unit. This stream contains most of the alkanol present in the column feed and also a significant amount of hydrocarbons. Typically this sidestream contains at least 30 wt-%, preferably at least 70 wt-% and in particular over 90% of the total alkanol feed to the second distiflation zone. Recycling of this stream to the reaction zone will result in improved isoolefin and alkanol conversion within the whole process unit. Since the pressure in tower 35 is maintained at higher level than in tower 24, a practically complete removal of alkanol from the bottom stream is achieved, which makes the resulting olefinic $C_4$ stream an attractive feedstock for any downstream processing unit requiring essentially oxygen free hydrocarbon feedstocks. Any water or dimethyl ether present in reaction effluent will go to the overhead product of distillation tower 35 whereas the minute amounts of DEE (diethyl ether) will go to the bottom product of column 24. By carefully designing column 24, virtually all ether product will remain in the bottom stream of tower 24. The columns 24 and 35 may be functionally built within one shell along the principles set in the previous example.

Another important application of the present invention is the production of pure TAME or TAEE.

In the TAME and/or TAEE case a stream containing reactive $C_5$ olefins (isoamylenes) and at least minor amounts of hydrocarbons from the adjacent groups (that is $C_4$ and $C_6$ hydrocarbons or at least some $C_4$ hydrocarbons) is fed to the etherification zone with a suitable alkanol and any hydrocarbon recycle stream destined for further etherification. After carrying out etherifying in the reaction section 21–23 according to principles analog to the previous examples, the resulting effluent is taken to a first distillation tower 24. The distillation is carried out in such a way that the ether product (TAME or TAEE for methanol and ethanol based ether products respectively) is taken out as a bottom product from the tower and the unreacted $C_5$ and lighter hydrocarbons ($C_4$'s) are recovered as a distillate. The alkanol will be partly or totally recovered as an overhead product. Depending on requirements and the relative amounts of $C_6$ hydrocarbons present in the feed these components may be recovered fully or partly as an overhead product.

The distillate is fed to a second distillation unit 35 in which light hydrocarbons ($C_4$'s and lighter) are recovered as an overhead product and $C_5$'s and any heavier hydrocarbons as an essentially alkanol free bottom product. The distillate contains the alkanol present in the column feed in concentrations dictated by pressure and the azeotropic constitution of the light hydrocarbon-alkanol mixture. If suitable amounts of the light component needed for the azeotrope are not present in the original feed stream, such a component may be added to the feed of the distillation tower or in any suitable location within the tower itself or in overhead or reboiling equipment of the column or to any suitable location in the process. Analogously to the previously presented example a side stream is taken from a suitably located point in the column and recycled to the reaction section of the process unit. This stream contains most of the alkanol present in the column feed and also a significant amount of reactive olefins. Recycling of this stream will result in improved iso-olefin and alkanol conversion within the whole process unit. Since the pressure in tower 35 is maintained at higher level than in tower 24, a practically complete removal of alcohol from the bottom stream is achieved, which makes the resulting olefinic $C_5$ stream an attractive feedstock for any downstream processing unit requiring essentially oxygen free hydrocarbon feedstocks. Any significant amount of water, dimethyl ether or diethyl ether present in reaction effluent will go to the overhead product of distillation tower 24. By carefully designing column 24, virtually all ether product will remain in the bottom stream of tower 24. The columns 24 and 35 may be functionally built within one shell along the principles set in the previous examples.

The following calculated examples will elucidate the invention:

EXAMPLE 1

Preparation of tertiary methyl ethers

Using the process configuration of FIG. 1, methyl ethers are prepared from an olefinic hydrocarbon feed as follows:

Distillation columns: Inner diameter 160 mm, height 11,000 mm, filled with column packing. The number of packing layers was 6.

Reactors: Inner diameter 154.1 mm, height 1,150 mm. Filled with the catalyst DOWEX M-32

Location of side drawoffs: Between the second and third packing layer.

Feed point of the first column: Between the fourth and fifth packing layer.

Feed point of the second column: Between the third and fourth packing layer.

An FCC $C_{4-7}$ cut containing 30 kg hydrocarbons/h (composition shown in Table 2) and methanol (amount shown in Table 2) are mixed together and heated. Then, side drawoff streams from the distillation columns are combined therewith and the modified feed stream thus obtained is conducted through the reactors. As a result of the exothermal etherification reaction, the temperature increases in the reactors by 1 to 20° C. The reaction mixture obtained is conducted to the first distillation column and subjected to distillation. The overhead is conducted to the second distillation column and subjected to ftrther distillation. Side streams are taken from both columns.

The feed temperature of each reactor is 40° C. and the temperatures of the reactor effluents are 55, 45 and 42° C., respectively.

The pressure of the side drawoff streams are increased with pumps before they are conducted to the reactors.

The reflux ratio of the first distillation zone is 1.8 and the pressure is 5 bar, whereas the reflux ratio of the second distillation zone is 60 and the pressure 14 bar.

The compositions of the various streams and products are shown in Table 2.

TABLE 2

|  | Feed | | MEOH feed | | Draw-off 1 | | Draw-off 2 | | Bottom 1 | | Top 1 | | Bottom 2 | | Top 2 | |
| --- | --- | --- | --- | --- | --- | --- | --- | --- | --- | --- | --- | --- | --- | --- | --- | --- |
|  | Mass | Mass- | Mass | Mass- | Mass | Mass- | Mass | Mass- | Mass | Mass- | Mass | Mass- | Mass | Mass- | Mass | Mass- |
| H2O | 0.00 | 0.00 | 0.00 | 0.05 | 0.00 | 0.00 | 0.00 | 0.00 | 0.00 | 0.00 | 0.00 | 0.00 | 0.00 | 0.00 | 0.00 | 0.00 |
| DME | 0.00 | 0.00 | 0.00 | 0.00 | 0.00 | 0.00 | 0.00 | 0.03 | 0.00 | 0.00 | 0.00 | 0.02 | 0.00 | 0.00 | 0.00 | 0.03 |
| trans-2-butene | 1.25 | 4.16 | 0.00 | 0.00 | 1.38 | 4.62 | 0.69 | 5.16 | 0.02 | 0.10 | 1.92 | 9.00 | 1.22 | 16.51 | 0.00 | 0.06 |
| 3-methyl-1-butene | 0.03 | 0.10 | 0.00 | 0.00 | 0.06 | 0.21 | 0.00 | 0.02 | 0.01 | 0.04 | 0.02 | 0.11 | 0.02 | 0.28 | 0.00 | 0.00 |
| Iso-pentane | 3.77 | 12.57 | 0.00 | 0.00 | 8.16 | 27.27 | 0.04 | 0.32 | 2.97 | 11.95 | 0.84 | 3.94 | 0.80 | 10.77 | 0.00 | 0.00 |
| 2-methyl-1-butene | 0.33 | 1.10 | 0.00 | 0.00 | 0.04 | 0.12 | 0.00 | 0.00 | 0.02 | 0.06 | 0.00 | 0.01 | 0.00 | 0.02 | 0.00 | 0.00 |
| n-pentane | 3.08 | 10.27 | 0.00 | 0.00 | 4.07 | 13.59 | 0.00 | 0.01 | 3.05 | 12.24 | 0.03 | 0.16 | 0.03 | 0.45 | 0.00 | 0.00 |

TABLE 2-continued

|  | Feed | | MEOH feed | | Draw-off 1 | | Draw-off 2 | | Bottom 1 | | Top 1 | | Bottom 2 | | Top 2 | |
| --- | --- | --- | --- | --- | --- | --- | --- | --- | --- | --- | --- | --- | --- | --- | --- | --- |
|  | Mass | Mass-% | Mass | Mass-% | Mass | Mass-% | Mass | Mass-% | Mass | Mass-% | Mass | Mass-% | Mass | Mass-% | Mass | Mass-% |
| 2-methyl-2-butene | 2.37 | 7.90 | 0.00 | 0.00 | 0.36 | 1.21 | 0.00 | 0.00 | 0.30 | 1.22 | 0.00 | 0.01 | 0.00 | 0.03 | 0.00 | 0.00 |
| n-pentene | 0.48 | 1.58 | 0.00 | 0.00 | 0.54 | 1.79 | 0.00 | 0.00 | 0.47 | 1.90 | 0.00 | 0.01 | 0.00 | 0.02 | 0.00 | 0.00 |
| 2,3-dimethyl-butene | 2.20 | 7.34 | 0.00 | 0.00 | 0.86 | 2.86 | 0.00 | 0.00 | 2.20 | 8.85 | 0.00 | 0.00 | 0.00 | 0.00 | 0.00 | 0.00 |
| 2-methyl-1-pentene | 0.48 | 1.60 | 0.00 | 0.00 | 0.09 | 0.29 | 0.00 | 0.00 | 0.25 | 1.01 | 0.00 | 0.00 | 0.00 | 0.00 | 0.00 | 0.00 |
| 3-methyl-pentene | 1.30 | 4.32 | 0.00 | 0.00 | 0.41 | 1.38 | 0.00 | 0.00 | 1.30 | 5.21 | 0.00 | 0.00 | 0.00 | 0.00 | 0.00 | 0.00 |
| MEOH | 0.00 | 0.00 | 2.75 | 99.95 | 3.98 | 13.31 | 0.80 | 5.92 | 0.00 | 0.00 | 0.80 | 3.77 | 0.00 | 0.00 | 0.01 | 1.50 |
| 2-methyl-2-pentene | 2.44 | 8.15 | 0.00 | 0.00 | 0.19 | 0.64 | 0.00 | 0.00 | 0.69 | 2.78 | 0.00 | 0.00 | 0.00 | 0.00 | 0.00 | 0.00 |
| N-hexane | 1.71 | 5.71 | 0.00 | 0.00 | 0.42 | 1.40 | 0.00 | 0.00 | 1.71 | 6.89 | 0.00 | 0.00 | 0.00 | 0.00 | 0.00 | 0.00 |
| benzene | 0.33 | 1.11 | 0.00 | 0.00 | 0.07 | 0.22 | 0.00 | 0.00 | 0.33 | 1.34 | 0.00 | 0.00 | 0.00 | 0.00 | 0.00 | 0.00 |
| TAME | 0.00 | 0.00 | 0.00 | 0.00 | 0.42 | 0.40 | 0.00 | 0.00 | 3.46 | 13.89 | 0.00 | 0.00 | 0.00 | 0.00 | 0.00 | 0.00 |
| 2-methyl-heksane | 1.31 | 4.36 | 0.00 | 0.00 | 0.13 | 0.45 | 0.00 | 0.00 | 1.31 | 5.26 | 0.00 | 0.00 | 0.00 | 0.00 | 0.00 | 0.00 |
| N-heptane | 1.50 | 4.99 | 0.00 | 0.00 | 0.10 | 0.35 | 0.00 | 0.00 | 1.50 | 6.01 | 0.00 | 0.00 | 0.00 | 0.00 | 0.00 | 0.00 |
| TAOH | 0.00 | 0.00 | 0.00 | 0.00 | 0.00 | 0.00 | 0.00 | 0.00 | 0.01 | 0.03 | 0.00 | 0.00 | 0.00 | 0.00 | 0.00 | 0.00 |
| THME | 0.00 | 0.00 | 0.00 | 0.00 | 0.08 | 0.27 | 0.00 | 0.00 | 2.73 | 10.98 | 0.00 | 0.00 | 0.00 | 0.00 | 0.00 | 0.00 |
| 4-methyl-hexene | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| Isobutylene | 1.60 | 5.33 | 0.00 | 0.00 | 0.03 | 0.09 | 0.04 | 0.31 | 0.00 | 0.00 | 0.06 | 0.28 | 0.02 | 0.26 | 0.00 | 0.04 |
| MTBE | 0.00 | 0.00 | 0.00 | 0.00 | 0.88 | 2.95 | 0.00 | 0.00 | 2.48 | 9.97 | 0.00 | 0.00 | 0.00 | 0.00 | 0.00 | 0.00 |
| Propane | 0.37 | 1.22 | 0.00 | 0.00 | 0.12 | 0.40 | 0.39 | 2.87 | 0.00 | 0.00 | 0.75 | 3.53 | 0.00 | 0.00 | 0.37 | 81.47 |
| Propylene | 0.01 | 0.03 | 0.00 | 0.00 | 0.00 | 0.01 | 0.01 | 0.04 | 0.00 | 0.00 | 0.01 | 0.06 | 0.00 | 0.00 | 0.01 | 1.75 |
| Isobutane | 2.37 | 7.90 | 0.00 | 0.00 | 4.02 | 13.42 | 7.79 | 57.81 | 0.02 | 0.07 | 10.14 | 47.55 | 2.29 | 30.97 | 0.06 | 13.04 |
| 1-Butene | 1.13 | 3.78 | 0.00 | 0.00 | 1.45 | 4.84 | 2.10 | 15.61 | 0.01 | 0.05 | 3.22 | 15.12 | 1.12 | 15.05 | 0.01 | 1.75 |
| 1,3-Butadiene | 0.04 | 0.13 | 0.00 | 0.00 | 0.04 | 0.15 | 0.05 | 0.39 | 0.00 | 0.00 | 0.09 | 0.43 | 0.64 | 0.52 | 0.00 | 0.03 |
| N-Butane | 0.75 | 2.49 | 0.00 | 0.00 | 0.84 | 2.80 | 0.64 | 4.78 | 0.02 | 0.06 | 1.38 | 6.45 | 0.73 | 9.88 | 0.00 | 0.13 |
| cis-2-Butene | 1.15 | 3.83 | 0.00 | 0.00 | 1.19 | 3.97 | 0.91 | 6.74 | 0.02 | 0.09 | 2.04 | 9.55 | 1.13 | 15.22 | 0.00 | 0.20 |
| Total | 30.00 | 100.00 | 2.75 | 100.00 | 29.93 | 100.00 | 13.47 | 100.00 | 24.90 | 100.00 | 21.32 | 100.00 | 7.41 | 100.00 | 0.45 | 100.0 |
| Pressure, kpa | 2400 | | 2400 | | 2400 | | 2400 | | 500 | | 500 | | 1400 | | 1400 | |
| Temperature, ° C. | 45.0 | | 35.0 | | 62.9 | | 81.2 | | 114.4 | | 40.5 | | 93.4 | | 45.3 | |

EXAMPLE 2

Preparation of ETBE

Using the process configuration of FIG. 2, ETBE is prepared from an olefinic hydrocarbon feed as follows:

Distillation columns: Inner diameter 160 mm, height 11,000 mm, filled with column packing. The number of packing layers was 6.

Reactors: Inner diameter 154.1 mm, height 1,150 mm. Filled with the catalyst DOWEX M-32

Location of side drawoff: Between the second and third packing layer.

Feed point of the first column: Between the fourth and fifth packing layer.

Feed point of the second column: Between the third and fourth packing layer.

An FCC $C_4$ cut containing 30 kg hydrocarbons/h (composition shown in Table 3) and ethanol (amount shown in Table 3) are mixed together and heated. Then, side drawoff streams from the distillation columns are combined therewith and the modified feed stream thus obtained is conducted through the reactors. As a result of the exothermal etherification reaction, the temperature increases in the reactors by 1 to 20° C., depending on the efficiency of the heat insulation. The reaction mixture obtained is conducted to the first distillation column and subjected to distillation. The overhead is conducted to the second distillation column and subjected to further distillation.

The feed temperature of each reactor is 40° C. and the temperatures of the reactor effluents are 52, 45 and 41° C., respectively.

The pressure of the side drawoff stream are increased with pumps before it is conducted to the reactors.

The reflux ratio of the first distillation zone is 1.8 and the pressure 5 bar, whereas the reflux ratio of the second distillation zone is 60 and the pressure 16 bar.

The compositions of the various streams and products are shown in Table 3.

TABLE 3

|  | Feed | | EtOH feed | | Side draw | | Bottom 1 | | Top 1 | | Top 2 | | Bottom 2 | |
| --- | --- | --- | --- | --- | --- | --- | --- | --- | --- | --- | --- | --- | --- | --- |
| Mass flow, kg/h | Mass | Mass-% | Mass | Mass-% | Mass | Mass-% | Mass | Mass-% | Mass | Mass-% | Mass | Mass-% | Mass | Mass-% |
| Propylene | 0.69 | 2.30 | 0.00 | 0.00 | 0.91 | 1.92 | 0.00 | 0.00 | 1.59 | 2.21 | 0.68 | 62.90 | 0.00 | 0.00 |
| Propane | 0.36 | 1.19 | 0.00 | 0.00 | 0.93 | 1.97 | 0.00 | 0.00 | 1.28 | 1.79 | 0.35 | 32.26 | 0.00 | 0.00 |
| i-Butane | 8.26 | 27.53 | 0.00 | 0.00 | 26.16 | 55.20 | 0.00 | 0.00 | 34.48 | 48.07 | 0.04 | 4.09 | 8.29 | 35.61 |

TABLE 3-continued

| Mass flow, kg/h | Feed | | EtOH feed | | Side draw | | Bottom 1 | | Top 1 | | Top 2 | | Bottom 2 | |
|---|---|---|---|---|---|---|---|---|---|---|---|---|---|---|
| | Mass | Mass-% | Mass | Mass-% | Mass | Mass-% | Mass | Mass-% | Mass | Mass-% | Mass | Mass-% | Mass | Mass-% |
| n-Butane | 2.41 | 8.04 | 0.00 | 0.00 | 2.48 | 5.23 | 0.00 | 0.00 | 4.88 | 6.81 | 0.00 | 0.04 | 2.40 | 10.32 |
| 1-Butene | 4.41 | 14.70 | 0.00 | 0.00 | 9.48 | 20.00 | 0.00 | 0.00 | 13.91 | 19.39 | 0.01 | 0.58 | 4.43 | 19.02 |
| cis-2-Butene | 3.83 | 12.77 | 0.00 | 0.00 | 2.96 | 6.24 | 0.00 | 0.00 | 6.78 | 9.45 | 0.00 | 0.02 | 3.82 | 16.41 |
| trans-2-Butene | 4.05 | 13.51 | 0.00 | 0.00 | 3.65 | 7.70 | 0.00 | 0.00 | 7.69 | 10.72 | 0.00 | 0.04 | 4.04 | 17.37 |
| Isobutene | 5.10 | 17.00 | 0.00 | 0.00 | 0.51 | 1.08 | 0.00 | 0.00 | 0.74 | 1.03 | 0.00 | 0.03 | 0.23 | 0.97 |
| i-Pentane | 0.62 | 2.08 | 0.00 | 0.00 | 0.01 | 0.02 | 0.55 | 5.63 | 0.08 | 0.11 | 0.00 | 0.00 | 0.07 | 0.30 |
| n-Pentane | 0.02 | 0.06 | 0.00 | 0.00 | 0.00 | 0.00 | 0.02 | 0.17 | 0.00 | 0.00 | 0.00 | 0.00 | 0.00 | 0.00 |
| 2-Methyl-1-butene | 0.09 | 0.30 | 0.00 | 0.00 | 0.00 | 0.00 | 0.01 | 0.07 | 0.00 | 0.00 | 0.00 | 0.00 | 0.00 | 0.00 |
| 2-Methyl-2-butene | 0.03 | 0.09 | 0.00 | 0.00 | 0.00 | 0.00 | 0.09 | 0.90 | 0.00 | 0.00 | 0.00 | 0.00 | 0.00 | 0.00 |
| 1-Pentene | 0.13 | 0.43 | 0.00 | 0.00 | 0.00 | 0.00 | 0.13 | 1.32 | 0.00 | 0.00 | 0.00 | 0.00 | 0.00 | 0.01 |
| EtOH | 0.00 | 0.00 | 4.15 | 100.00 | 0.31 | 0.64 | 0.05 | 0.51 | 0.31 | 0.43 | 0.00 | 0.03 | 0.00 | 0.00 |
| ETBE | 0.00 | 0.00 | 0.00 | 0.00 | 0.00 | 0.00 | 8.90 | 91.04 | 0.00 | 0.00 | 0.00 | 0.00 | 0.00 | 0.00 |
| TAEE | 0.00 | 0.00 | 0.00 | 0.00 | 0.00 | 0.00 | 0.03 | 0.35 | 0.00 | 0.00 | 0.00 | 0.00 | 0.00 | 0.00 |
| Total | 30.00 | 100.00 | 4.15 | 100.00 | 47.39 | 100.00 | 9.77 | 100.00 | 71.75 | 100.00 | 1.08 | 100.00 | 23.27 | 100.00 |
| Pressure, kPa | 2500 | | 2500 | | 2500 | | 500 | | 500 | | 1600 | | 1600 | |
| Temperature, °C. | 25 | | 25 | | 88.6 | | 124.2 | | 38.5 | | 41.2 | | 95.8 | |

EXAMPLE 3

Preparation of TAME

Except for the following changes, TAME is prepared from an FCC $C_5$ cut by repeating Example 2:

The feed temperature of each reactor is 40° C. and the temperatures of the reactor effluents are 58, 42 and 40.5° C., respectively. The reflux ratio of the first distillation zone is 0.6 and the pressure is 4 bar, whereas the reflux ratio of the second distillation zone is 60 and the pressure 9 bar.

The compositions of the various streams and products are shown in Table 4.

TABLE 4

| | Feed | | MeOH feed | | Bottom 1 | | Top 1 | | Bottom 2 | | Top 2 | | Side draw | |
|---|---|---|---|---|---|---|---|---|---|---|---|---|---|---|
| | Mass | Mass-% | Mass | Mass-% | Mass | Mass-% | Mass | Mass-% | Mass | Mass-% | Mass | Mass-% | Mass | Mass-% |
| Water | 0.00 | 0.00 | 0.00 | 0.05 | 0.00 | 0.00 | 0.00 | 0.00 | 0.00 | 0.00 | 0.00 | 0.00 | 0.00 | 0.00 |
| di-methyl-ether | 0.00 | 0.00 | 0.00 | 0.00 | 0.00 | 0.00 | 0.00 | 0.00 | 0.00 | 0.00 | 0.00 | 0.05 | 0.00 | 0.00 |
| trans-2-butene | 1.31 | 4.38 | 0.00 | 0.00 | 0.00 | 0.00 | 7.55 | 9.22 | 0.00 | 0.01 | 1.31 | 85.05 | 6.24 | 10.61 |
| 3-ethyl-1- | 0.09 | 0.29 | 0.00 | 0.00 | 0.00 | 0.00 | 1.49 | 1.82 | 0.07 | 0.34 | 0.01 | 0.93 | 1.41 | 2.39 |
| iso-pentane | 10.77 | 35.91 | 0.00 | 0.00 | 0.01 | 0.14 | 40.42 | 49.32 | 10.66 | 49.27 | 0.10 | 6.21 | 29.66 | 50.47 |
| 2-methyl-1- | 0.94 | 3.15 | 0.00 | 0.00 | 0.00 | 0.00 | 0.13 | 0.15 | 0.04 | 6.18 | 0.00 | 0.01 | 0.09 | 0.15 |
| N-pentane | 8.76 | 29.18 | 0.00 | 0.00 | 0.03 | 0.27 | 18.09 | 22.07 | 8.72 | 40.30 | 0.00 | 0.26 | 9.36 | 15.93 |
| 2-methyl-2- | 6.77 | 22.57 | 0.00 | 0.00 | 0.01 | 0.05 | 1.60 | 1.95 | 0.80 | 3.68 | 0.00 | 0.01 | 0.80 | 1.36 |
| N-pentene | 1.36 | 4.52 | 0.00 | 0.00 | 0.01 | 0.11 | 2.81 | 3.43 | 1.35 | 6.22 | 0.00 | 0.02 | 1.47 | 2.50 |
| MeOH | 0.00 | 0.00 | 3.25 | 99.95 | 0.00 | 0.00 | 9.86 | 12.04 | 0.00 | 0.00 | 0.12 | 7.46 | 9.75 | 16.58 |
| TAME | 0.00 | 0.00 | 0.00 | 0.00 | 10.00 | 99.31 | 0.00 | 0.00 | 0.00 | 0.00 | 0.00 | 0.00 | 0.00 | 0.00 |
| TAOH | 0.00 | 0.00 | 0.00 | 0.00 | 0.01 | 0.09 | 0.00 | 0.00 | 0.00 | 0.00 | 0.00 | 0.00 | 0.00 | 0.00 |
| 4-methyl-hexene | 0.00 | 0.00 | 0.00 | 0.00 | 0.00 | 0.02 | 0.00 | 0.00 | 0.00 | 0.00 | 0.00 | 0.00 | 0.00 | 0.00 |
| Total | 30.00 | 100.00 | 3.26 | 100.00 | 10.07 | 100.00 | 81.96 | 100.00 | 21.64 | 100.00 | 1.54 | 100.00 | 58.77 | 100.00 |
| Pressure. kPa | 2400 | | 2400 | | 400 | | 400 | | 900 | | 900 | | 900 | |
| Temperature, °C. | 40 | | 25 | | 138,9 | | 65,7 | | 114,8 | | 77,7 | | 94,8 | |

We claim:

1. A process for preparing an ether product containing at least one tertiary alkyl ether, said process comprising the steps of reacting isoolefins of an isoolefinic hydrocarbon feedstock containing at least two groups of $C_{3-7}$ hydrocarbons having different carbon numbers in a reaction zone with at least one alkanol to form an ether-containing reaction mixture, subjecting said ether-containing reaction mixture to distillation in a first distillation zone, recovering an ether product from the bottom of the first distillation zone, withdrawing an overhead stream from the first distillation zone containing unreacted alkanol and a mixture of hydrocarbons comprising at least the two lightest hydrocarbon groups present in the feedstock, conducting the overhead stream to a second distillation zone and subjecting it to distillation, withdrawing from the second distillation zone an overhead product, which contains the lightest hydrocarbons of the overhead stream of the first distillation zone and the minimum amount of alkanol typically due to azeotropic behaviour of the mixture, withdrawing a side drawoff from the second distillation zone and recirculating it to the reaction zone, and recoving a bottoms product from the second distillation zone.

2. The process according to claim 1, wherein the second distillation is operated so that the amount of lightest hydrocarbons contained in the overhead product of the second distillation zone corresponds essentially to the amount of the same hydrocarbons in the hydrocarbon feedstock.

3. The process according to claim 1 or 2, wherein the side drawoff from the second distillation zone contains most of the unreacted alkanol of the overhead stream of the first distillation zone.

4. The process according to claim 3, wherein the alkanol in the overhead stream of the first distillation zone is present in an amount 0.05 to 30 wt-% of the hydrocarbon-alkanol-mixture and the second distillation zone is operated at a higher pressure than the first distillation zone.

5. The process according to claim 4, wherein the second distillation zone is operated at a pressure at least 1 bar higher than the first distillation zone.

6. The proces according to ciaim 5, wherein the second distillation zone is operated at a pressure of at least 4 bars higher than the first distillation zone.

7. The process according to claim 5, wherein the flow rate of the side drawoff from the second distillation zone is 1 to 1000% of the flow of the total hydrocarbon feedstock.

8. The process according to claim 7, wherein the flow rate of the flow rate is 50 to 200%.

9. (The process according to claim 1, wherein the bottoms product of the second distillation zone contains the heaviest group of hydrocarbons of the overhead stream of the first distillation zone.

10. The process according to claim 9, wherein the bottoms product of the second distillation zone contains only trace amounts of oxygenates.

11. The process according to claim 1, wherein the feed alkanol is methanol and wherein the overhead product of the second distillation zone comprises dimethyl ether and water.

12. The process according to claim 10, wherein the bottoms product of the second distillation zone is fed to alkylation, oligomerization, polymerization or dehydrogenation without separate oxygenate removal.

13. The process according to claim 1, which comprises
feeding the reaction mixture to the first distillation column,
withdrawing a side drawoff from the column, and
recirculating the side drawoff to the reaction zone.

14. The process according to claim 13, wherein the hydrocarbon feedstock and the side drawoff of the distillation are combined before the reaction zone to form a modified feed for the reaction zone.

15. The process according to claim 13 or 14, wherein the flow rate of the side drawoff is 1 to 1000% of the flow of the total hydrocarbon feedstock.

16. The process according to claim 15, wherein the flow rate of the side drawoff is 50 to 200% of the flow of the total hydrocarbon feedstock.

17. The process according to claim 15, wherein a mixed ether product is prepared comprising at least one member selected from the group consisting of ethyl and methyl ethers of isobutylene, isoamylenes and tertiary $C_{6+}$ isoolefins.

18. The process according to claim 1, wherein the bottom product or side drawoff of the second distillation zone is subjected to distillation in a third distillation zone.

19. The process according to claim 18, wherein the bottoms product of the third distillation zone is combined with the bottom product of the first distillation zone and/or recirculated to the reaction zone.

20. The process according to claim 1, wherein the reaction mixture from the reaction zone is subjected to distillation in a predistillation zone, and the overhead stream of the predistillation zone is subjected to further distillation in the second distillation zone and the bottoms stream to further distillation in the first distillation zone.

21. The process according to claim 1, wherein a side drawoff of the second distillation zone is fed to alkylation, oligomerization, polymerization or dehydrogenation without separate oxygenate removal.

22. The process according to claim 1, wherein the first distillation zone and at least a part of the reaction zone are arranged in a catalytic distillation column.

23. The process according to claim 1 for preparing an ether product containing tertiary amyl alkyl ethers, wherein the second distillation zone is arranged in a catalytic distillation column.

24. The process according to claim 1, wherein the hydrocarbon feedstock comprises treated or untreated: FCC gasoline, FCC light gasoline, FCC liquefied petroleum gas, Pyrolysis $C_5$ gasoline, $C_4$ stream (raffinate 1) from steam cracking unit, olefinic $C_4$ stream from a butane dehydrogenating unit, TCC gasoline, $C_4$ stream from TCC, RCC gasoline, $C_4$ stream from RCC, coker gasoline or $C_4$ stream originating from a coking unit or a mixture of these.

25. The process according to claim 24, wherein the feedstock further comprises a $C_{2-4}$ hydrocarbon.

26. The process according to claim 25, wherein the $C_{2-4}$ hydrocarbon is separately fed into the etherification process.

27. A process for preparing an ether product, which comprises
subjecting an olefinic hydrocarbon feed containing isobutylene and at least 0.1 wt-% $C_3$ hydrocarbons to etherification with methanol or ethanol, respectively, in a reaction zone to form a reaction mixture,
recovering the reaction mixture and conducting it to a first distillation zone, wherein it is subjected to distillation,
withdrawing from the first distillation zone an overhead stream containing a mixture of unreacted $C_3$ and $C_4$ hydrocarbons and unreacted alkanol,
recovering from the first distillation zone a bottoms product containing the tertiary butyl ether,
subjecting the overhead stream from the first distillation zone to distillation in a second distillation zone,
withdrawing from the second distillation zone an overhead stream containing a mixture of unreacted $C_3$ hydrocarbons and 0.05–30% alkanol, calculated from the weight of said mixture,
withdrawing a side drawoff from the second distillation zone and recirculating it to the reaction zone, and
recovering from the second distillation zone a bottoms product containing an essetially oxygenate-free $C_4$ hydrocarbon fraction.

28. The process according to claim 27, wherein the hydrocarbon feedstock comprises treated or untreated: FCC liquefied petroleum gas, $C_4$ stream (raffinate 1) from steam cracking unit, olefinic $C_4$ stream from a butane dehydrogenating unit, $C_4$ stream from TCC, $C_4$ stream from RCC, or $C_4$ stream originating from a coking unit or a mixture thereof.

29. A process for preparing an ether product, which comprises
subjecting an olefinic hydrocarbon feed containing isoamylenes and at least 0.1 wt-% $C_4$ hydrocarbons to etherification with methanol or ethanol, respectively, in a reaction zone to form a reaction mixture,
recovering the reaction mixture and conducting it to a first distillation zone, wherein it is subjected to distillation,
withdrawing from the first distillation zone an overhead stream containing a mixture of unreacted $C_4$ and $C_5$ hydrocarbons and unreacted alkanol, recovering from the first distillation zone a bottoms product containing the tertiary amyl ether, subjecting the overhead stream of the first distillation zone to distillation in a second distillation zone, withdrawing from the second distillation zone an overhead stream containing a mixture of unreacted $C_4$ hydrocarbons and 0.05 to 30% of alkanol, calculated from the weight of said mixture, recovering a second bottoms product containing an essentially oxygente-free $C_5$ hydrocarbofraction, and withdrawing a side drawoff and recirculating it to the reaction zone.

30. The process according to claim 29, wherein the hydrocarbon feedstock comprises treated or untreated: FCC gasoline, FCC light gasoline, Pyrolysis $C_5$ gasoline from steam cracking unit, TCC gasoline, RCC gasoline or coker gasoline or a mixture of these.

31. A process for preparing an ether product containing a mixture of tertiary alkyl ethers, which comprises subjecting an olefinic $C_3$ to $C_7$ hydrocarbon feed containing reactive isoolefins to etherification with an alkanol in a reaction zone to form a reaction mixture containing tertiary $C_4$ to $C_7$ alkyl ethers, recovering the reaction mixture and conducting it to a first distillation zone, wherein it is subjected to distillation, withdrawing from the first distillation zone an overhead stream mainly containing a mixture of unreacted $C_3$ to $C_4$ hydrocarbons and unreacted alkanol, recovering from the first distillation zone a bottoms product containing tertiary alkyl ethers and $C_{5+}$ hydrocarbons, withdrawing from the first distillation zone a side drawoff and recirculating it to the reaction zone, subjecting the overhead stream of the first distillation zone to distillation in a second distillation zone, withdrawing from the second distillation zone a overhead stream containing a mixture of unreacted $C_3$ hydrocarbons and 0.05 to 30% alkanol, calculated from the weight of said mixture, recovering from the second distillation zone a bottoms product containing an essentially oxygenate-free $C_4$ hydrocarbon fraction, and withdrawing from the second distillation zone a second side drawoff and recirculating it to the reaction zone.

32. The process according to claim 31, wherein the hydrocarbon feedstock comprises treated or untreated: FCC gasoline, FCC light gasoline, FCC liquefied petroleum gas, Pyrolysis $C_5$ gasoline, $C_4$ stream (raffinate 1) from steam cracking unit, olefinic $C_4$ stream from a butane dehydrogenating unit, TCC gasoline, $C_4$ stream from TCC, RCC gasoline, $C_4$ stream from RCC, coker gasoline or $C_4$ stream originating from a coking unit or a mixture thereof.

33. The process according to any one of claims 27 to 32, wherein the overhead stream of the first distillation zone contains the minimum amount of alkanol typically due to azeotropic behaviour of the hydrocarbon-alkanol mixture, and the second distillation zone is operated at a higher pressure than the first distillation zone.

34. The process according to claim 33, wherein the first distillation zone and at least a part of the reaction zone are arranged in a reactive distillation column.

35. The process according to any one of claims 27 to 32, wherein the second distillation zone is arranged in a reactive distillation column.

36. The process according to any one of claims 27 to 32, wherein the feedstock further comprises a $C_{2-4}$ hydrocarbon.

37. The process according to claim 36, wherein the $C_{2-4}$ hydrocarbon is separately fed into the etherification process.

* * * * *